US008569056B2

(12) United States Patent
Kosaka

(10) Patent No.: US 8,569,056 B2
(45) Date of Patent: Oct. 29, 2013

(54) METHOD FOR PRODUCING RETINAL NEUROCYTE FROM NEURAL STEM CELL DERIVED FROM IRIS TISSUE

(75) Inventor: Mitsuko Kosaka, Okayama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1775 days.

(21) Appl. No.: 10/559,784

(22) PCT Filed: Jun. 11, 2004

(86) PCT No.: PCT/JP2004/008222
§ 371 (c)(1),
(2), (4) Date: Dec. 8, 2005

(87) PCT Pub. No.: WO2004/111213
PCT Pub. Date: Dec. 23, 2004

(65) Prior Publication Data
US 2006/0134280 A1 Jun. 22, 2006

(30) Foreign Application Priority Data
Jun. 11, 2003 (JP) .................................. 2003-166646

(51) Int. Cl.
*C12N 5/071* (2010.01)
*C12N 5/00* (2006.01)
*G01N 33/53* (2006.01)

(52) U.S. Cl.
USPC ............. 435/368; 435/7.1; 435/325; 435/377

(58) Field of Classification Search
None
See application file for complete search history.

(56) References Cited

FOREIGN PATENT DOCUMENTS

| JP | 2002-112764 | 4/2002 |
|---|---|---|
| JP | 2002-325571 | 11/2002 |
| JP | 2003-325167 | 11/2003 |
| WO | WO 01/58460 | 8/2001 |

OTHER PUBLICATIONS

Mokry et al. Acta Med 50: 35-41, 2007.*
Pick et al. Stem Cells 25: 2206-2214, 2007.*
Amemiya et al. Biochem Biophys Res Comm 316:1-5, 2004.*
Dan-King Hu et al., "Isolation and Cultivation of Human Iris Pigment Epithelium", Investigative Ophthalmology & Visual Science, vol. 33, No. 8, Jul. 1992, pp. 2443-2453.
Norbert Kociok et al., "The mRNA Expression of Cytokines and their Receptors in Cultures Iris Pigment Epithelial Cells: A Comparison with Retinal Pigment Epithelial Cells" Experimental Eye Research, Academic Press Ltd., 1998, pp. 237-250.
Supplementary European Search Report.
Temple, S., "The Development of Neural Stem Cells", Nature vol. 414, Nov. 1, 2001 pp. 112-117.
Ahmad, I. et al., "Identification of Neural Progenitors in the Adult Mammalian Eye", Biochem. and Biophys. Res. Commun. vol. 270 (2000), pp. 517-521.
Zhao, S. et al., "In Vitro Transdifferentiation of Embryonic Rat Retinal Pigment Epithelium to Neural Retina", Brain Research vol. 677 (1995) pp. 300-130.
Dutt, K. et al., "Transdifferentiation of Adult Human Pigment Epithelium into Retinal Cells by Transfection with an Activated H-ras Proto-Oncogene", DNA and Cell Biology vol. 12, No. 8, (1993) pp. 667-673.
Zhao, X. et al., "Differentiation of Embryonic Stem Cells into Retinal Neurons", Biochem. and Biophys. Res. Commun. vol. 297 (2002), pp. 177-184.
Turner, D.L. et al., "A Common Progenitor for Neurons and Glia Persists in Rat Retina Late in Development", Nature vol. 328, Jul. 9, 1987, pp. 131-136.
Akagi, T. et al., "Different Characteristics of Rat Retinal Progenitor Cells from Different Culture Periods", Neuroscience Letters 341 (2003) pp. 213-216.
Reynolds, B.A. and Weiss, S., "Generation of Neurons and Astrocytes from Isolated Cells of the Adult Mammalian Central Nervous System", Science, vol. 255, Mar. 27, 1992, pp. 1707-1710.
Layer, P.G. et al., "Inductive Effects of the Retinal Pigmented Epithelium (RPE) on Histogensis of the Avian Retina as Revealed by Retinospheroid Technology", Seminars in Cell & Developmental Biology, vol. 9 (1998) pp. 257-262.
Hoperskaya, Olga A. et al., "Transdifferentiation of Adult Frog Iris in Retina or Lens by Exogenous Influences", Develop. Growth and Differ., vol. 23, No. 3 (1981) pp. 201-213.
Tropepe, Vincent et al., "Retinal Stem Cells in the Adult Mammalian Eye", Science, vol. 287, Mar. 17, 2000, pp. 2032-2036.
Kosaka, Mitsuko et al., "In Vitro Culture System for Iris-Pigmented Epithelial Cells for Molecular Analysis of Transdifferentiation", Experimental Cell Research 245, Article No. EX984211 (1998) pp. 245-251.
Haruta, Mastoshi et al., "Induction of Photoreceptor-Specific Phenotypes in Adult Mammalian Iris Tissue", Nature Neuroscience, vol. 4, No. 12, Dec. 2001, pp. 1163-1164.
International Search Report dated Sep. 7, 2004 for corresponding Application No. PCT/JP2004/008222 (English & Japanese Translations).
Supplementary Partial European Search Report dated Jun. 1, 2006 for Application No. 04745816.1 corresponding to PCT/JP2004/008222.
Kano, T. et al. , "Protective effect against ischemia and light damage of iris pigment epithelial cells transfected with the BDNF gene," Invest. Ophthalmol. Vis. Sci. vol. 43, Dec. 2002.

(Continued)

Primary Examiner — Daniel E Kolker
Assistant Examiner — Aditi Dutt
(74) Attorney, Agent, or Firm — Edwards Wildman Palmer LLP; David G. Conlin

(57) ABSTRACT

A method for producing retinal nerve cells by inducing differentiation of iris pigmented epithelial cells into the retinal nerve cells. In a first method, iris pigmented epithelial cells derived from a mammal and embryo retinal stem cells derived from a bird are co-cultured. In a second method, iris pigmented epithelial cells of a bird or a mammal is isolated, and the iris pigmented epithelial- cells is subjected to adherent culturing. According to these methods, the retinal nerve cells can be produced by using iris pigmented epithelial cells collected from a patient per se. Therefore, there is a possibility that highly effective regenerative medical treatment can be realized.

4 Claims, 7 Drawing Sheets

(56) References Cited

OTHER PUBLICATIONS

Layer, P.G., et al., "Pigmented epithelium sustains cell proliferation and decreases expression of opsins and acetylcholinesterase in reaggregated chicken retinospheroids," Eur. J. Neuroscience Vo. 9, 1795-1803 (1997).

Office Action mailed on Feb. 13, 2009 by the Canadian Patent Office in Serial No. 2,528,426.

Office Action mailed on Mar. 17, 2009 by the Japanese Patent Office in patent application No. 2005-506941 (including English translation of same).

Y. Ikegami et al., "Neural Cell Differentiation from Retinal Pigment Epithelial Cells of the Newt: An Organ Culture Model for the Urodele Retinal Regeneration", *Journal of Neurobiology*, vol. 50, pp. 209-220 (2002).

* cited by examiner

METHOD FOR PRODUCING RETINAL NEUROCYTE FROM NEURAL STEM CELL DERIVED FROM IRIS TISSUE

TECHNICAL FIELD

The present invention relates to a method for producing retinal nerve cells by inducing differentiation of neural stem/progenitor cells derived from iris tissue of a mammal and a bird. The present invention also relates to retinal nerve cells obtained by the method.

BACKGROUND ART

Recently, it has been found that a brain and a spinal cord have neural stem/progenitor cells, and it has been reported that ES (embryonic stem) cells are differentiated into specific central nervous system cells. This has raised expectations for central nervous system regenerative medical treatment. Further, as a process for isolating and selectively culturing the neural stem/progenitor cells, a neurosphere method (floated coagulated mass culturing technique) has been established. Furthermore, a method for inducing differentiation of the neural stem/progenitor cells has been reported which is designed to induce differentiation of the neural stem/progenitor cells into neural cells by culturing a sphere (aggregate) made from the neural stem/progenitor cells by adherent culturing after the floated coagulated mass culturing technique.

Further, it has been reported that by transplanting into a living organism neural stem/progenitor cells derived from a brain or a spinal cord, or ES cells, the transplanted cells are differentiated into specific nerve cells as a result of adaptation to the environment (see Non-Patent Document 1: *Nature* 414, p. 112-117, review, 2001).

Incidentally, when retinal nerve cells of a mammal are once degenerated, the retinal nerve cells cannot be regenerated, so that functions of the retinal nerve cells are impaired. Furthermore, degeneration of visual cells due to a retinal degeneration disease or the like may lead to loss of sight. At present, there is no effective treatment for such an intractable disease. Accordingly, if the retinal nerve cells can be produced by differentiation induction of the neural stem/progenitor cells as described above, a highly effective regenerative medical treatment will be realized.

As the neural stem/progenitor cells used to induce differentiation into the retinal nerve cells, ciliary epithelial cells and retinal pigmented epithelial cells have been used so far. The retinal pigmented epithelial cells and the ciliary epithelial cells are derived from neural plates. The photoreceptor layer is coated with the retinal pigmented epithelial cells. The photoreceptor layer is an outermost cell layer of a retina including a plurality of cell layers. A ciliary epithelium is tissue which lies between an iris and a retina.

For example, reported in Non-Patent Document 2 (*Science* 287, p. 2032-2035, 2000) is a method for inducing differentiation by culturing, according to the adherent culturing, spheres (aggregates) which have been formed by culturing ciliary epithelial cells according to the floated coagulated mass culturing technique. Also in Non-Patent Document 3 (*Biochem. and Biophys. Res Commun.* 270, p517-521, 2000), it has been reported that there is a possibility that differentiation of the ciliary epithelial cells into retinal nerve cells can be induced.

Further, in Non-Patent Document 4 (*Brain Res.* 677 (2), p. 300-310, 1995), it is reported by a culturing experiment that retinal pigmented epithelial cells of a mammal are differentiable into nerve cells, albeit in a limited portion of a fetal period. Note that, also in Non-Patent Document 5 (*DNA Cell Biol* 12 (8), p. 667-673, 1993), it has been reported that there is a possibility that differentiation of retinal pigmented epithelial cells into retinal nerve cells can be induced.

If neural stem/progenitor cells, derived from a brain or a spinal cord, and ES cells, are used to regenerative medical treatment, the use raises many problems such as immunological rejection caused by cell transportation, ethical issues, and unbalance between demand and supply of transplant cell sources. If it becomes possible to use, as a transplant source, cells derived from a transplant recipient per se, it will pave a way to autogenous transplantation, thus solving the foregoing problems.

However, in view of medical applications, an idea of using ciliary epithelial cells as materials for central nervous system regeneration is unrealistic, because it is very difficult to obtain the ciliary epithelial cells from a patient per se.

Further, Non-Patent Document 4 states that, for mammals, differentiability into nerve cells is observed only in retinal pigmented epithelial cells in a limited time within a fetal period in which many relatively undifferentiated cells exist. That is, relatively-undifferentiated cells rarely exist in tissue of an adult mammal. Since retinal pigmented epithelial cells of an adult is also highly differentiated, it is difficult to isolate and culture the retinal pigmented epithelial cells. Therefore, at present, it is impossible to use the retinal pigmented epithelial cells of the adult mammal as materials for central nervous system regeneration.

Further, although a method for producing retinal nerve cells from ES cells is reported in Non-Patent Document 6 (*Biochem. and Biophys. Res. Commun.* 297, p. 117-184, 2000), the method is extremely inefficient.

Under such circumstances, iris pigmented epithelial cells of an eyeball are one example of cells expected to serve as materials for central nervous system regeneration. The iris pigmented epithelial cells are a component of an iris that opens and narrows a pupil in accordance with an amount of light so as to adjust an amount of light which reaches a retina. Like the retinal pigmented epithelial cells and the ciliary epithelial cells, the iris pigmented epithelial cells are derived from neural plates. Since it is sufficiently possible to collect part of iris pigmented epithelial cells from a patient per se, the iris pigmented epithelial cells can be effectively utilized as regenerative materials capable of autologous transplantation.

It has been deemed difficult to isolate and culture iris pigmented epithelial cells due to a small number of iris pigmented epithelial cells and a small number of tissues formed therefrom. However, the inventors have reported that the inventors have successfully isolated and cultured iris pigmented epithelial cells of a chick (Non-Patent Document 7: *Experimental Cell Res.* 245, p. 245-251, 1998). In Non-Patent Document 7, a culturing experiment shows that iris pigmented epithelial cells of the chick are capable of being differentiated into lenses.

Furthermore, the inventors have made it possible to isolate and culture iris cells of a mammal (mouse, rat, or human embryo) by a method improved from the process of Non-Patent Document 7 (see Non-Patent Document 8: *Nature Neuroscience* 4 (12), p. 1163, 2001).

In Non-Patent Document 8, primary culturing of isolated iris tissue of an adult rat was carried out, and although it was confirmed that some cells expressed neural markers, no specifically differentiated neural marker was detected. It was confirmed that the cultured iris cells form a rhodopsin protein necessary for a photoreceptor function, when in order to obtain visual cells of a retina, the cultured iris cells were forced to express Crx gene, which is suggested to play an important role in a period during which the visual cells are generated.

In Non-Patent Document 8, differentiation into the visual cells is induced only in the case where Crx gene, which is a specific gene, is expressed. However, when medical applications are taken into consideration, it is not preferable to induce differentiation by expressing a gene because inducing differentiation by expressing a gene involves a risk of damaging DNA.

Therefore, at present, no method has been established which, by inducing differentiation of neural stem/progenitor cells (iris pigmented epithelial cells) derived from iris tissue, produces retinal nerve cells which can be effectively used for regenerative medical treatment.

As described above, it is possible to collect part of iris pigmented epithelial cells from a patient per se. Therefore, if retinal nerve cells are obtained by inducing differentiation of iris pigmented epithelial cells, then regenerative medical treatment which uses cells of a patient per se will be realized. Moreover, it is expected that an important contribution will be brought about to establishing treatment for a retinal degeneration disease for which there is no effective treatment at present.

The present invention has been completed in consideration of the foregoing problems and has as an object to provide a method for producing retinal nerve cells by inducing differentiation into retinal nerve cells, without requiring gene transfer, from iris pigmented epithelial cells which may be effectively used for regenerative medical treatment, and the retinal nerve cells obtained by the method.

DISCLOSURE OF INVENTION

As a result of diligently studying the foregoing problems, the inventors have found that by co-culturing embryonic retinal stem cells and iris pigmented epithelial cells or by conducting adherent culturing of the iris pigmented epithelial cells in a culture medium, differentiation of the iris pigmented epithelial cells into retinal nerve cells can be induced without conducting gene transfer. Thus, the inventors have completed the present invention.

A method of the present invention for producing retinal nerve cells includes the steps of: co-culturing embryonic retinal stem cells and iris pigmented epithelial cells; and inducing differentiation of the iris pigmented epithelial cells into the retinal nerve cells.

According to the method of the present invention for producing the retinal nerve cells, the iris pigmented epithelial cells and the embryonic retinal stem cells are co-cultured, so that differentiation into the retinal nerve cells can be induced without conducting gene transfer like a conventional process (see Non-Patent Document 8). Therefore, the retinal nerve cells obtained by the producing method of the present invention can be used as materials for regenerative medical treatment without posing such a risk as DNA damage and can be effectively utilized in regenerative medical treatment.

Further, as described above, since part of iris pigmented epithelial cells can be collected from a patient per se, the retinal nerve cells can be obtained from the iris pigmented epithelial cells derived from the patient by the producing method of the present invention, and regenerative medical treatment using cells of a patient per se can be realized This makes it possible to overcome such problems of regenerative medical treatment as immunological rejection, ethical issues, and unbalance between the demand and supply of transplant cell sources. Moreover, it is expected that a contribution will be brought about to establishing a treatment for retinal degeneration disease for which there is no effective treatment at present.

Further, the retinal-nerve-cell-producing method of the present invention is arranged so that the iris pigmented epithelial cells are derived from a mammal.

According to the foregoing method, it is possible to produce retinal nerve cells of the mammal for which no conventional effective retinal-nerve-cell-differentiation-inducing method has been found. Moreover, the method can be widely applied to the fields of medicine, biotechnology, and the like.

Further, the retinal-nerve-cell-producing method of the present invention is arranged so that the embryonic retinal stem cells are derived from a bird.

According to the forgoing method, since the iris pigmented epithelial cells of the bird and that of the mammal have a characteristic of responding to the same factor, differentiation can be satisfactorily induced when the retinal nerve cells are produced from the iris pigmented epithelial cells of the mammal. Further, the embryonic retinal stem cells of the bird can be isolated easier and obtained in larger quantity than that of the mammal, and therefore have an advantage of being used easily.

Further, the method for producing the retinal nerve cells is arranged so that the iris pigmented epithelial cells are isolated from an eyeball and then selectively cultured by a floated coagulated mass culturing technique.

According to the foregoing method, the isolated iris pigmented epithelial cells are selectively cultured by the floated coagulated mass culturing technique so as to obtain an aggregate similar to an aggregate (sphere) made from neural stem/progenitor cells. Therefore, the method can be preferably used to produce the retinal nerve cells by inducing differentiation of the iris pigmented epithelial cells.

Note that, as described later, the aggregate of the iris pigmented epithelial cells is cultured in a culture medium mixed with a publicly known conventional growth factor, so that differentiation of the aggregate into nerve cells can be induced. That is, it can be said that the iris pigmented epithelial cells are relatively undifferentiated. Further, the iris pigmented epithelial cells can also be called "neural stem/progenitor cells derived from iris tissue."

Further, the method for producing the retinal nerve cells is arranged so that the isolation of the iris pigmented epithelial cells includes: an iris-tissue-extirpating step extirpating iris tissue from the eyeball; and an iris-pigmented-epithelium-separating step of separating an iris pigmented epithelium from the iris tissue thus extirpated.

According to the method, it can be ensured that the iris pigmented epithelial cells are isolated and effectively differentiated into the retinal nerve cells.

Further, the retinal nerve cells of the present invention can be obtained by any one of the foregoing methods.

The retinal nerve cells are produced from the iris pigmented epithelial cells part of which can be collected from a patient per se and therefore make it possible to realize regenerative medical treatment using cells of a patient per se. Moreover, this makes it possible to overcome such problems of regenerative medical treatment as immunological rejection, ethical issues, and unbalance between the demand and supply of transplant cell sources.

Further, since the iris pigmented epithelial cells are produced by inducing differentiation without gene transfer, it does not pose a risk such as DNA damage and ensures safety when used for medical purposes.

Furthermore, another method of the present invention for producing retinal nerve cells includes the steps of: isolating iris pigmented epithelial cells from an eyeball; and performing adherent culturing of the iris pigmented epithelial cells in a serum-free culture medium so as to induce differentiation of the iris pigmented epithelial cells into the retinal nerve cells.

According to the method for producing the retinal nerve cells, adherent culturing of the iris pigmented epithelial cells is carried out with a serum-free culture medium, so that differentiation into the retinal nerve cells can be induced without conducting gene transfer like a conventional process (see Non-Patent Document 8). Therefore, the retinal nerve cells obtained by the producing method of the present invention can be used as materials for regenerative medical treatment without posing such a risk as DNA damage and can be effectively utilized in regenerative medical treatment.

Further, as described above, since part of the iris pigmented epithelial cells can be collected from a patient per se, the retinal nerve cells can be obtained from the iris pigmented epithelial cells derived from the patient by the producing method of the present invention, and regenerative medical treatment using cells of a patient per se can be realized. Moreover, it is possible to overcome such problems of regenerative medical treatment as immunological rejection, ethical issues, and unbalance between the demand and supply of transplant cell sources. Therefore, it is expected that the method will contribute to establishing a treatment for retinal degeneration disease for which there is no effective treatment at present.

Further, the producing method using adherent culturing is arranged so that the iris pigmented epithelial cells are derived from a bird or a mammal.

According to the foregoing method, as described later in the Example, it is possible to obtain various retinal nerve cells such as retinal visual cells, bipolar cells, and Muller glia cells.

Further, the method of the present invention for producing the retinal nerve cells is arranged so that the serum-free culture medium when the adherent culturing starts contains at least one of FGF2, FGF9, and CNTF with a concentration in a range of 1 to 100 ng/ml.

According to the foregoing method, the serum-free culture medium contains the factor with a concentration of 1 to 100 ng/ml, so that differentiation into the retinal nerve cells can be induced more securely, and productivity of the retinal nerve cells can be improved. Note, in the present invention, that two or all of the three factors may be contained. Also in this case, it is preferable that each factor has a concentration of 1 to 100 ng/ml.

Further, the method of the present invention for producing the retinal nerve cells is arranged so that the iris pigmented epithelial cells in the serum-free culture medium at the start of the adherent culturing has a cell density of $1 \times 10^5$ cells/cm$^2$ or less.

According to the foregoing method, the iris pigmented epithelial cells in the serum-free culture medium at the start of the adherent culturing has a cell density of $1 \times 10^5$ cells/cm$^2$ or less, so that differentiation into the retinal nerve cells can be induced more securely, and productivity of the retinal nerve cells can be more improved.

Furthermore, a further method of the present invention for producing retinal nerve cells includes the steps of: isolating iris pigmented epithelial cells from an eyeball; starting adherent culturing by implanting the iris pigmented epithelial cells in a culture medium containing FGF2 and/or FGF9; and after the step of starting the adherent culturing, inducing differentiation of the iris pigmented epithelial cells into the retinal nerve cells by performing the adherent culturing of the iris pigmented epithelial cells by using the culture medium to which CNTF is added and from which FGF2 and/or FGF9 is removed.

According to the further producing method using adherent culturing, in addition to the effect obtained by the above-mentioned producing method using adherent culturing, differentiation into the retinal nerve cells can be induced more quickly.

The further producing method using adherent culturing may be arranged so that when the culture medium is a serum-free culture medium in the step of starting the adherent culturing, a serum is further added to the culture medium in the step of inducing the differentiation into the retinal nerve cells.

Further, retinal nerve cells of the present invention can be obtained by any one of the foregoing methods using adherent culturing.

Since part of the iris pigmented epithelial cells can be collected from a patient per se, the retinal nerve cells can be obtained from the iris pigmented epithelial cells derived from the patient by the producing method of the present invention, and regenerative medical treatment using cells of a patient per se can be realized. Therefore, it is possible to overcome such problems of regenerative medical treatment as immunological rejection, ethical issues, and unbalance between the demand and supply of transplant cell sources.

Further, since the retinal nerve cells are produced by inducing differentiation without gene transfer, it does not pose a risk such as DNA damage and ensures safety when used for medical purposes.

For a fuller understanding of the nature and advantages of the invention, reference should be made to the ensuing detailed description taken in conjunction with the accompanying drawings.

BRIEF DESCRIPTION OF DRAWINGS

FIG. 7(*b*) is a pattern diagram illustrating iodopsin positive cells derived from the iris pigmented epithelial cells of the chick. The white area indicates iodopsin subjected to immunostaining in the Example.

FIG. 7(*c*) is a pattern diagram HPC-1 positive cells derived from the iris pigmented epithelial cells of the chick. The white area indicates HPC-1 subjected to immunostaining in the Example.

BEST MODE FOR CARRYING OUT THE INVENTION

[First Embodiment]

A First Embodiment of the present invention will be described below with reference to FIGS. 1, 2, 4(*a*), and 4(*b*). The present invention is not to be limited by the description.

Described in the First Embodiment is a method for producing retinal nerve cells by co-culturing embryonic retinal stem cells and iris pigmented epithelial cells and then inducing differentiation of the iris pigmented epithelial cells into the retinal nerve cells.

Figure 1:
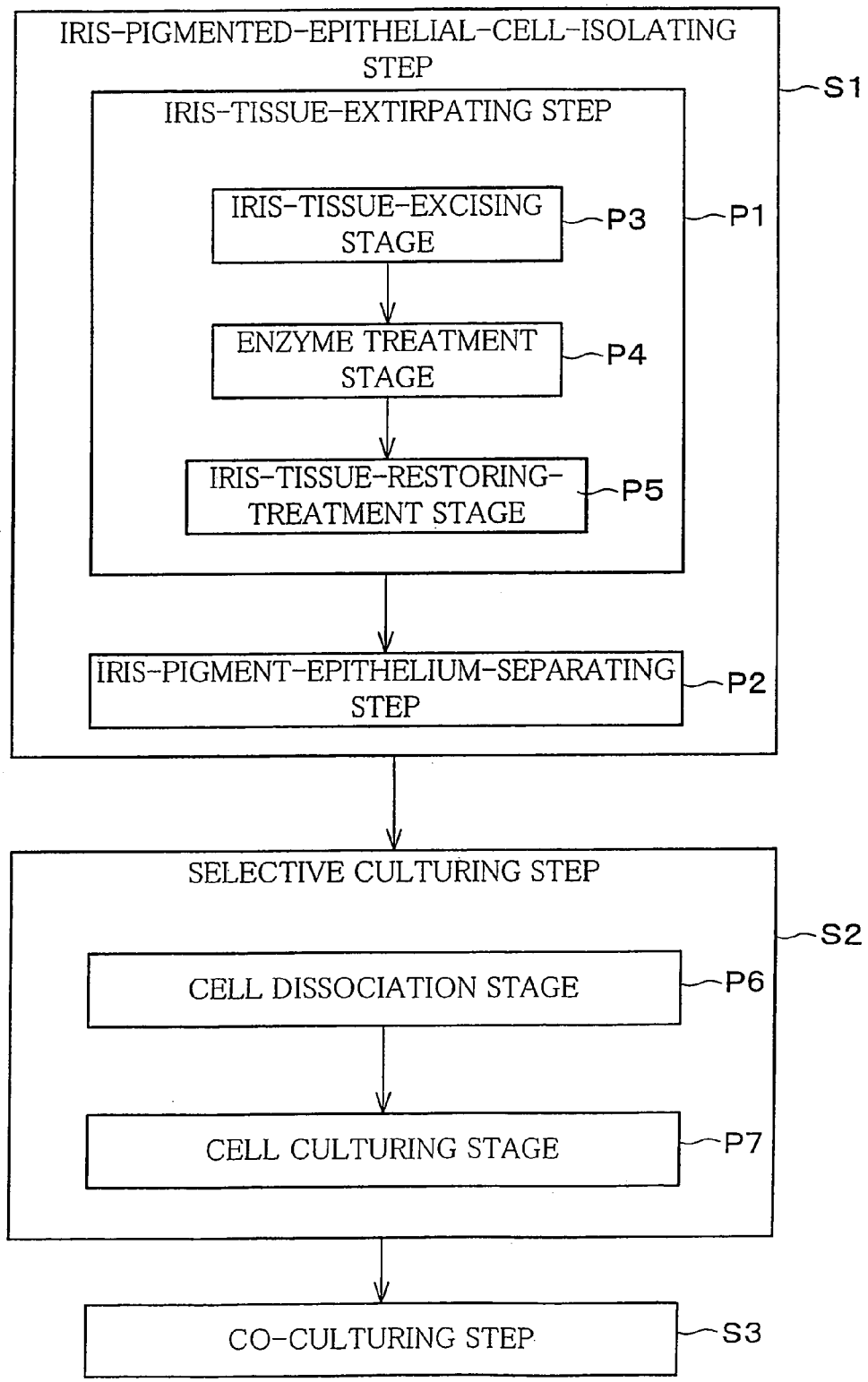
FIG. 1 is a schematic flow chart illustrating one embodiment of a method according to the present invention for producing retinal nerve cells.

FIG. 1 schematically illustrates steps of a method according to the present embodiment for producing retinal nerve cells. As shown in FIG. 1, the method is roughly divided into three steps. A first step is an iris-pigmented-epithelial-cell-isolating step S1, in which iris pigmented epithelial cells are isolated from an eyeball of an animal. A second step is a selective culturing step S2, in which the isolated iris pigmented epithelial cells are selectively cultured according a floated coagulated mass culturing technique. A third step is a co-culturing step S3, in which the iris pigmented epithelial cells selectively cultured and embryonic retinal stem cells are co-cultured.

That is, in the method according to the present invention for producing the retinal nerve cells, the iris pigmented epithelial cells are differentiated into the retinal nerve cells by conducting the co-culturing step S3 of co-culturing the iris pigmented epithelial cells and the embryonic retinal stem cells, the iris pigmented epithelial cells being obtained by conducting the iris-pigmented-epithelial-insolating step S1 and then the selective culturing step S2 of selectively culturing the iris pigmented epithelial cells. As a result, the retinal nerve cells can be obtained. Because the iris pigmented epithelial cells obtained in the selective culturing step S2 are relatively undifferentiated and can be differentiated into various nerve cells, the iris pigmented epithelial cells can be called "neural stem/progenitor cells derived from iris tissue."

Further, in the present embodiment, the iris pigmented epithelial cells used to produce the retinal nerve cells are isolated from an eyeball of an animal and then selectively cultured by the floated coagulated mass culturing technique as described above. This makes it possible to obtain aggregates similar to aggregates (spheres) made from neural stem/progehitor cells derived from a brain or a spinal cord.

In the following, the embryonic retinal stem cells used in the method will be described.

The embryonic retinal stem cells, identified by Reference 1 (Turner DL & Cepko, *Nature* (1987) 328: p. 131-136), are undifferentiated cells differentiable into the retinal nerve cells. The embryonic retinal stem cells can be isolated from retinal tissue of an embryo by a publicly known conventional process. The isolation can be conducted for example by a method described in Reference 2 (Akagi T. et. al, *Neurosi Lett.*, May 8, 2003, 341 (3): p. 213-216).

The embryonic retinal stem cells can be collected from any animal species. However, in case of producing the retinal nerve cells by using the iris pigmented epithelial cells derived from a mammal, it is preferable that the embryonic retinal stem cells be collected and isolated from retinal tissue of a mammal or a bird. Furthermore, it is more preferable to use embryonic retinal stem cells derived from a bird. This is because the embryonic retinal stem cells derived from a bird can be collected from a developing egg, and thus they can be isolated relatively easily and inexpensively and obtained in large quantity. It is even more preferable to use embryonic retinal stem cells derived from a chicken among other birds.

Further, the iris pigmented epithelial cells used for the method of the present embodiment for producing the retinal nerve cells can be collected from any animal species. However, because it is desired to apply the producing method to animals for which no conventional effective retinal-nerve-cell-differentiation-inducing method has been found, it is preferable that the iris pigmented epithelial cells be derived from a mammal. Moreover, it is preferable to use iris pigmented epithelial cells derived from a rodent such as a mouse, a rat, a hamster, or a house mouse since a rodent serves many uses as a laboratory animal. When medical application is taken into consideration, it is preferable to use iris pigmented epithelial cells derived from an animal (e.g., a ferret or a monkey) having a developed visual function or from a human being.

In the following, the method for isolating and culturing the iris pigmented epithelial cells, i.e., the iris-pigmented-epithelial-cell-isolating step S1 and the selective culturing step. S2 will be described more in detail.

As shown in FIG. 1, the iris pigmented epithelial cells can be isolated and cultured by the method including at least: an iris-pigmented-epithelial-cell-isolating step (Step 1; hereinafter, Step is abbreviated as S) of isolating iris pigmented epithelial cells from the eyeball; and a selective culturing step S2 of selectively culturing the isolated iris pigmented epitheiial cells by the floated coagulated mass culturing technique. According to this method, it is possible to obtain aggregates similar to aggregates (spheres) made from neural stem/progenitor cells derived from a brain or a spinal cord.

Here, the iris pigmented epithelial cells can be isolated from a mammal of any age between a fetal period and an adult period. That is, iris pigmented epithelial cells derived from an adult mammal, as well as iris pigmented epithelial cells derived from a fetal animal, can be used as materials for the method according to the present embodiment for producing the retinal nerve cells.

The iris-pigmented-epithelial-cell-isolating step S1 is not particularly limited in terms of techniques and other features. concretely adopted therein as long as the iris pigmented epithelial cells are isolated. Generally speaking, a publicly known conventional process may be adopted so as to extirpate iris tissue from the eyeball of the mammal and isolate the iris pigmented epithelial cells from the extirpated iris tissue. It is preferable to use a process described in Non-Patent Document 8 so as to extirpate the iris tissue from the eyeball of the mammal.

The selective culturing process S2 is not particularly limited in terms of techniques and other features concretely adopted therein as long as the iris pigmented epithelial cells isolated from the eyeball of the mammal can be selectively cultured. Generally speaking, a publicly known conventional process may be adopted so as to selectively culture only the iris pigmented epithelial cells isolated from the eyeball of the mammal.

The iris-pigmented-epithelial-cell-isolating step S1 includes at least an iris-tissue-extirpating step (Process 1; hereinafter, Process is abbreviated as P) and an iris-pigment-epithelium-separating step P2.

Further, as shown in FIG. 1, the iris-tissue-extirpating step P1 further includes: an iris-tissue-excising stage P3 of excising only iris tissue from the eyeball of the mammal; an enzyme treatment stage P4 of subjecting the excised iris tissue to enzyme treatment; and an iris-tissue-restoring-treatment stage P5 of restoring the enzyme-treated iris tissue.

Moreover, the selective culturing step S2 at least includes: a cell dissociation stage P6 of dissociating into individual cells the iris pigmented epithelial cells, isolated in the iris-pigmented-epithelial-cell-isolating step S1, which are in an aggregation state; and a cell culturing stage P7 of selectively culturing only the isolated iris pigmented epithelial cells.

In the following, the stages P3 to P5 of the iris-tissue-extirpating step P1 will be described in detail. First, the iris-tissue-excising stage P3 is not particularly limited in terms of techniques and other features adopted therein as long as only iris tissue can be excised from the eyeball of the mammal. Generally speaking, a publicly known conventional technique may be adopted so as to excise only iris tissue from the eyeball of the mammal. For example, the iris-tissue-excising stage P3 can be conducted by using commercially available micro scissors.

The enzyme treatment stage P4 is for subjecting the iris tissue to enzyme treatment so as to make it easy to dissociate the iris pigmented epithelial cells from the iris tissue. The enzyme treatment stage P4 is not particularly limited in terms of techniques and other features adopted therein. Generally speaking, a publicly known conventional technique may be adopted so as to conduct the stage.

For example, the enzyme treatment stage P4 can be conducted by allowing the iris tissue to react for 15 to 40 minutes in a dispase solution containing a commercially available dispase and then allowing the iris tissue to react for 20 to 30 minutes in an EDTA solution containing commercially available EDTA (ethylenediaminetetraacetic acid). The enzyme treatment stage P4 is not particularly limited in terms of enzymes and reagents used therein, and a publicly known conventional enzyme and reagent may be used which can treat the iris tissue so that it will be easy to dissociate the iris pigmented epithelial cells from the iris tissue.

The iris-tissue-restoring-treatment stage P5 is for restoring the iris tissue weakened by enzyme treatment. The iris-tissue-restoring-treatment stage P5 is not particularly limited in terms of techniques and other features adopted therein, and a publicly known conventional technique may be adopted so as to conduct the stage.

For example, after the reaction at the enzyme treatment stage, the iris-tissue-restoring-treatment stage P5 can be conducted by allowing the iris tissue to react for 30 to 60 minutes in a culture medium containing a commercially available fetal calf serum. The iris-tissue-restoring-treatment stage P5 is not particularly limited in terms of serum-containing culture mediums and reagents used, and a culture medium and reagent may be used which contain a publicly known conventional serum capable of restoring the weakened iris tissue.

Further, in the iris-tissue-extirpating step (P1), the reaction time at the enzyme treatment stage P4 and the reaction time at the iris-tissue-restoring-treatment stage P5 are particularly important. By adjusting the reaction time during which the iris tissue is allowed to react in the dispase solution at the enzyme treatment stage P4, the reaction time during which the iris tissue is allowed to react in the EDTA solution at the enzyme treatment stage P4, and the reaction time during which the iris tissue is allowed to react in the fetal-calf-serum-containing culture medium at the iris-tissue-restoring-treatment stage P5, an iris pigmented. epithelium can be separated not only from an eyeball of a chicken but also from an eyeball of an animal such as a mouse, a rat, or a human being.

In the following, the conditions for each of the animals will be described in detail.

In case of isolating iris pigmented epithelial cells from an eyeball of a mouse, it is preferable to allow iris tissue to react in 1000 U/ml dispase solution at 25 to 37° C. for 15 to 40 minutes, then in 0.05 to 0.1% EDTA solution at room temperature for 16 to 40 minutes, and then in a culture medium with 8 to 10% fetal calf serum content for 30 to 120 minutes.

Further, in case of isolating iris pigmented epithelial cells from an eyeball of a ten-day-old mouse, it is particularly preferable to allow iris tissue to react in 1000 U/ml dispase solution at 37° C. for 16 minutes, then in 0.05% EDTA solution at room temperature for 20 minutes, and then in a culture medium with 8% fetal calf serum content for 90 minutes.

Further, in case of isolating iris pigmented epithelial cells from an eyeball of a twelve-day-old mouse, it is particularly preferable to allow iris tissue to react in 1000 U/ml dispase solution at 37° C. for 20 minutes, then in 0.05% EDTA solution at room temperature for 25 minutes, and then in a culture medium with 8% fetal calf serum content for 60 minutes.

Further, in case of isolating iris pigmented epithelial cells from an eyeball of a two-month-old mouse, it is particularly preferable to allow iris tissue to react in 1000 U/ml dispase solution at 37° C. for 30 minutes, then in 0.05% EDTA solution at room temperature for 40 minutes, and then in a culture medium with 8% fetal calf serum content for 30 minutes.

In case of isolating iris pigmented epithelial cells from an eyeball of a rat, it is preferable to allow iris tissue to react in 1000 U/ml dispase solution at 37° C. for 15 to 40 minutes, then in 0.05 EDTA solution at room temperature for 15 to 60 minutes, and then in a culture medium with 8 to 10% fetal calf serum content for 30 to 120 minutes.

In case of isolating iris pigmented epithelial cells from an eyeball of a human embryo, it is preferable to allow iris tissue to react in 500 to 1000 U/ml dispase solution at 25 to 37° C. for 15 to 30 minutes, then in 0.05 to 0.1% EDTA solution at room temperature for 15 to 40 minutes, and then in a culture medium with 8 to 10% fetal calf serum content for 10 to 60 minutes.

Further, in case of isolating iris pigmented epithelial cells from an eyeball of a nineteen-week-old human embryo, it is particularly preferable to allow iris tissue to react in 1000 U/ml dispase solution at 37° C. for 30 minutes, the in 0.05% EDTA solution at room temperature for 30 minutes, and then in a culture medium with 8% fetal calf serum content for 60 minutes.

As the culture medium, for example, a DMEM medium (manufactured by Invitrogen Corporation) with a commercially available fetal calf serum of an appropriate amount can be used.

The iris-pigment-epithelium-separating step P2 is not particularly limited in terms of techniques and other features adopted therein as long as only an iris pigmented epithelium is separated from the iris tissue, which has been extirpated in the iris-tissue-extirpating step P1 and is made from an iris substrate and an iris pigmented epithelium. Generally speaking, a publicly known conventional technique may be adopted so as to separate only an iris pigmented epithelium from the iris tissue.

For example, the iris-pigment-epithelium-separating step P2 may be conducted by peeling only an iris pigmented epithelium from the restored iris tissue by using commercially available micro forceps.

In the following, the stages P6 and P7 of the selective culturing step S2 will be described in detail. First, the cell dissociation stage P6 is not limited in terms of techniques and other features adopted therein as long as sheet-like cells of the isolated iris pigmented epithelium are dissociated into individual cells. Generally speaking, a publicly known conventional technique may be adopted so as to dissociate sheet-like cells of the isolated iris pigmented epithelium into individual cells.

For example, at the cell dissociation stage P6, sheet-like cells of the isolated iris pigmented epithelium is dissociated into individual cells by using a commercially available trypsin solution. Further, for example, at the cell dissociation stage P6, sheet-like cells of the isolated iris pigmented epithelium can also be dissociated into individual cells by pipetting operation using a commercially available micro pipette instead of the trypsin solution.

The cell dissociation stage P6 is not particularly limited in terms of reagents and instruments used therein, and a publicly known conventional reagent and instrument may be used which make it possible to dissociate isolated iris pigmented epithelial cells in a aggregating state into individual cells.

The cell culturing stage P7 is not particularly limited in terms of techniques and other features adopted therein as long as the isolated iris pigmented epithelial cells can be selectively cultured. Generally speaking, a publicly known technique may be adopted so as to selectively culture the isolated iris pigmented epithelial cells. It is preferable to use a neurosphere method (floated coagulated mass culturing technique), described in Reference 3 (Science 1992: 225; 1707-1710), so as to selectively culture only the iris pigmented epithelial cells isolated from the eyeball of the mammal.

For example, at the cell culturing stage P7, a mixture of a commercially available serum-free culture medium and a commercially available N2 supplement is used as a culture medium. The iris pigmented epithelial cells dissociated at the cell dissociation stage P6 is cultured in a floated-coagulated-mass-culturing culture medium while rotated by using a commercially available shaker. This makes it possible to obtain aggregates similar to aggregates (spheres) made from neural stem/progenitor cells derived from a brain or a spinal cord.

The cell culturing stage P7 is not particularly limited in terms of culture mediums and reagents used therein, and a publicly known conventional culture medium and reagent may be used which make it possible to obtain aggregates similar to aggregates (spheres) made from neural stem/progenitor cells derived from a brain or a spinal cord.

The thus obtained aggregate derived from the iris pigmented epithelial cells is co-cultured with embryonic retinal stem cells.

Described in the following is the co-culturing step S3 of co-culturing the iris pigmented epithelial cells and the embryonic retinal stem cells, the iris pigmented epithelial cells being selectively cultured in the selective culturing step S2.

The co-culturing step S3 can be conducted for example in accordance with a method described in Reference 4 (*Semin Cell Dev Biol* (1998), 9 (3), p. 257-262, review). That is, when embryonic retinal stem cells derived from a bird such as a chicken are subjected to passage, the iris pigmented epithelial cells (neural stem/progenitor cells derived from the iris tissue) isolated from and dissociated from the eyeball of the mammal by the foregoing process are also subjected to passage together. In this way, the embryonic retinal stem cells and the iris pigmented epithelial cells are co-cultured. This makes it possible to induce differentiation of the mammal-derived iris pigmented epithelial cells into the retinal nerve cells.

Specifically, for example, in case of isolating iris tissue from an eyeball of a mouse and culturing iris pigmented epithelial cells, it is only necessary to conduct the isolation and the culturing in accordance with the foregoing procedures (i.e., the iris-pigmented-epithelial-cell-isolating step S1 and the selective culturing step S2, respectively). Thereafter, after three to six days of culturing, cells are dissociated by using a mixed solution of dispase and trypsin. Furthermore, the dissociated iris pigmented epithelial cells are introduced into a co-culturing system (see Reference 4) together with the embryonic retinal stem cells derived from the bird, and are subjected to rotation culturing. This makes it possible to obtain the retinal nerve cells differentiated from the iris pigmented epithelial cells.

Figure 2:
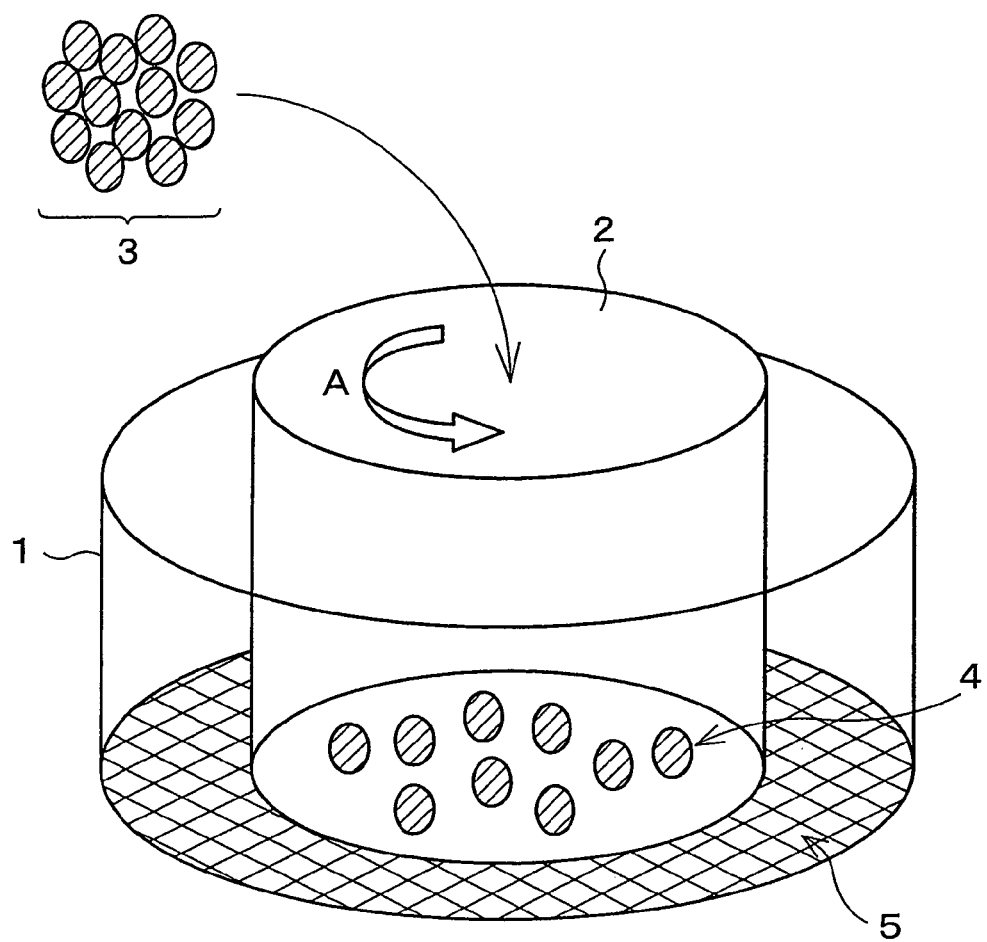
FIG. 2 is a pattern diagram illustrating a co-culturing system used in a co-culturing step of the method illustrated in FIG. 1.

FIG. 2 is a pattern diagram showing a co-culturing system used in the present embodiment. The co-culturing system, as shown in FIG. 2, includes a culture dish 1 and an inner well 2, disposed in the culture dish 1, which can be rotated in the direction of the arrow A. Moreover, in the co-culturing step S3, iris pigmented epithelial cells 5 derived from a bird is laid on a bottom of the culture dish 1, and embryonic retinal stem cells 3 derived from the bird and iris pigmented epithelial cells 3 derived from a mammal are injected into the inner well 2, In this way, a rotation culturing is conducted.

It is preferable to conduct the rotation culturing at 36.5 to 37.5° C. for 10 to 30 days at 50 to 70 rpm.

For example, by detecting a marker protein (which is specific to the retinal nerve cells) by staining it with an antibody specific thereto, it is possible to check whether or not the differentiation into the retinal nerve cells has been induced and thereby the retinal nerve cells have been produced in the cells co-cultured under such culturing conditions.

As the marker protein, rhodopsin or iodopsin can be exemplified which serves as a highly specific protein that gives a photoreceptor function. Rhodopsin is a protein necessary for a retinal visual cell, i.e., a type of retinal nerve cell to exhibit the photoreceptor function, and is specifically expressed in a rod forming the retinal visual cell. Iodopsin is also a protein necessary for the retinal visual cell to exhibit the photoreceptor function, and is specifically expressed in a cone forming the retinal visual cell. Further, as another marker protein, a vimentin can be used which detects Muller glia cells, i.e., a type of retinal nerve cell.

Detection of rhodopsin (or iodopsin) in the co-cultured cells (see FIG. 4(*a*)) confirms that differentiation of the cultured cells into the retinal nerve cells (more specifically retinal visual cells) has been induced. Further, detection of vimentin from the co-cultured cells (see FIG. 4(*b*)) confirms that differentiation of the cultured cells into retinal nerve cells (more specifically Muller glia cells) has been induced.

According to the method according to the present embodiment, as will be shown later in an Example, it is possible to surely induce the differentiation of the iris pigmented epithelial cells of a mammal into the retinal nerve cells, and thereby to produce retinal nerve cells.

In the present embodiment, retinal pigmented epithelial cells and embryonic retinal stem cells are derived from a bird and iris pigmented epithelial cells are derived from a mammal, but the present invention is not limited there. That is, for example, the differentiation of the iris pigmented epithelial cells into retinal nerve cells may be inducted by co-culturing the cells, all of which are derived from the mammal.

According to the foregoing method, it is possible to produce retinal nerve cells by inducing differentiation of iris pigmented epithelial cells into the retinal nerve cells. Therefore, the method has a possibility of being applicable for such highly effective regenerative medical treatment that retinal nerve cells are produced from part of iris tissue collected from a retinal disease patient per se.

[Second Embodiment]

A Second Embodiment of the present invention will be described below with reference to FIGS. 3 and 5(a) to 5(c). The present invention is not to be limited to the description.

Described in the Second Embodiment is a retinal nerve-cell-producing method which includes the steps of: isolating iris pigmented epithelial cells from an eyeball; and subjecting the iris pigmented epithelial cells to adherent culturing in a serum-free culture medium and inducing differentiation of the iris pigmented epithelial cells into retinal nerve cells.

Figure 3:
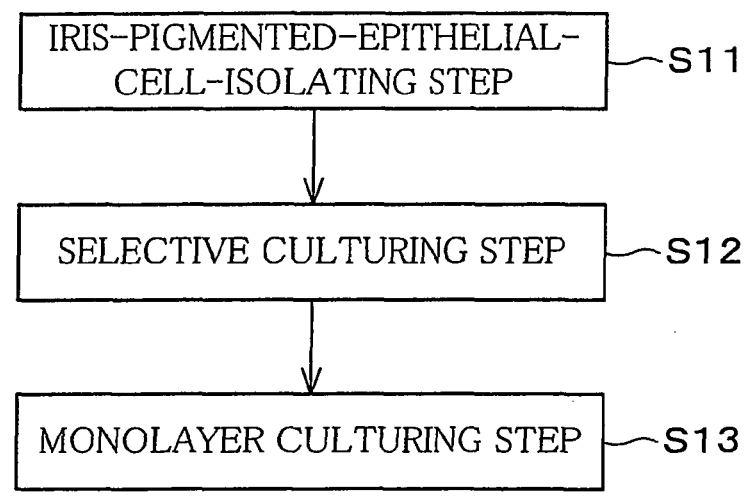
FIG. 3 is a schematic flow chart illustrating another embodiment according to the present invention for producing retinal nerve cells.

The method according to the present embodiment for producing the retinal nerve cells, as shown in FIG. 3, mainly includes: an iris-pigmented-epithelial-cell-isolating step S11 of isolating the iris pigmented epithelial cells from the eyeball; and an adherent culturing step S13 of performing adherent culturing of the iris pigmented epithelial cells.

Since the iris-pigmented-epithelial-cell-isolating step S11 can be conducted by the same technique as the iris-pigmented-epithelial-cell-isolating step S1 (see FIG. 1) described in the First Embodiment, the description thereof is omitted in the Second Embodiment.

Furthermore, the method according to the present embodiment for producing the retinal nerve cells includes a selective culturing step S12 between the iris-pigmented-epithelial-cell-isolating step S11 and the adherent culturing step S13. The selective culturing step S12 is equivalent to the selective culturing step (S2; see FIG. 1) described in the First Embodiment. Since the selective culturing step S12 can also be conducted by the same technique as the selective culturing step (S2; see FIG. 1) in the First Embodiment, the description thereof is omitted in the Second. Embodiment.

Moreover, in the selective culturing step S12, the iris-tissue-derived nerve cells (i.e., iris pigmented epithelial cells) are selectively cultured. Then, in the adherent culturing step S13, differentiation of the cultured iris pigmented epithelial cells into the retinal nerve cells is induced.

The iris pigmented epithelial cells cultured in the selective culturing step S12 are relatively undifferentiated and can be differentiated into various nerve cells. Here, the term "various nerve cells" encompasses neurons (nerve cells) and glia cells (non-neuronal cells). Glia cells do not exhibit an active electric response, which is one of characteristics of neurons. Glia cells, however, have various functions for neurons, such as supporting neurons and supplying nourishment to neurons. In case of a vertebrate animal, the glia cells are categorized by their functions and characteristics into four types: astroglia (astrocytes), microglia, oligodendroglia (oligodendrocytes), and Schwann cells.

Moreover, in the adherent culturing step S13 of the method according to the present embodiment for producing the retinal nerve cells, differentiation of the iris pigmented epithelial cells into neurons, astrocytes, oligodendrocytes is induced, and further differentiation of part of the neurons, astrocytes, and/or oligodendrocytes into retinal nerve cells is induced.

An animal species from which iris pigmented epithelial cells used for differentiation induction in the Second Embodiment are collected is not particularly limited. Examples of the animal species include birds (e.g., a chicken (including a chick), a quail, and the other birds) and mammals (e.g., a mouse, a rat, a human being, and other mammals). As will be described later in the Example, when iris pigmented epithelial cells derived from a bird or a mammal is used to produce retinal nerve cells by the producing method according to the Second Embodiment, various retinal nerve cells such as retinal visual cells, bipolar cells, and Muller glia cells can be obtained.

Particularly, there is no effective method at present for inducing differentiation to produce retinal nerve cells of a mammal. Therefore, it can be said that there is a high possibility for the method according to the present embodiment to be used, for example, in regenerative medical treatment of retinal nerve cells, because this method can induce the retinal nerve cells by using the iris pigmented epithelial cells derived from a mammal.

Further, in the First Embodiment, the iris pigmented epithelial cells of the mammal are isolated and cultured by the method including the iris-pigmented-epithelial-cell-isolating step and the selective culturing step. The same method can be applied for isolating and culturing iris pigmented epithelial cells of a bird.

For isolating the iris pigmented epithelial cells from an eyeball, the iris-pigmented-epithelial-cell-isolating step S11 is arranged so that the enzyme treatment and the iris-tissue-restoring treatment are conducted in the iris-tissue-extirpating step P1 (see FIG. 1) as described in the First Embodiment.

Here, for isolating an iris pigmented epithelium from an eyeball of a bird, it is preferable that the enzyme treatment and the iris-tissue-restoring treatment be conducted under such conditions that iris tissue is allowed to react in 1000 U/ml dispase solution at 36.5 to 37.5° C. for 10 to 40 minutes and then in 0.05 to 0.1% EDTA solution at room temperature for 20 to 50 minutes.

Further, in case of isolating an iris pigmented epithelium from an eyeball of a chick, it is preferable that iris tissue be allowed to react in 1000 U/ml dispase solution at 36.5 to 37.5° C. for 30 minutes, then in 0.05 to 0.1% EDTA solution at room temperature for 20 to 40 minutes, and then in a culture medium with 5 to 10% fetal calf serum content for 5 to 10 minutes.

Described below in detail is the adherent culturing step S13 of performing adherent culturing of the iris pigmented epithelial cells.

In the adherent culturing step S13, the adherent culturing of the iris pigmented epithelial cells is carried out with a serum-free culture medium. In the adherent culturing, a publicly known conventional adherent culturing process may be used. For example, the adherent culturing process described in Reference 3 may be used. The adherent culturing step S13 is not particularly limited in terms of culture media used therein as long as a serum-free culture medium is used, and a publicly known conventional culture medium may be used which makes it possible to induce differentiation of iris-pigmented-epithelial-cell-derived neural stem/progenitor cells into neural cells.

For example, as the culture medium used in the adherent culturing step S13, DMEM/F12 culture medium, DMEM culture medium, EMEM culture medium (all manufactured by Invitrogen Corporation), and other media can be exemplified.

Further, the adherent culturing step S13 is not particularly limited in terms of culture dishes and additive factors used therein, and a publicly known conventional culture dish and factor may be used which make it possible to induce differentiation of iris-pigmented-epithelial-cell-dehived neural stem/progenitor cells into neural cells.

Further, it is preferable that a serum-free culture medium at the start of the adherent culturing contain at least one of FGF2

(fibroblast growth factor 2), FGF9 (fibroblast growth factor 9) and CNTF (ciliary neurotrophic factor) with a concentration of 1 to 100 ng/ml and, more preferably, 10 to 40 ng/ml.

Moreover, it is preferable that, among the factors, the FGF2 and FGF9 stop being added after two to five days of culturing. That is, it is preferable to use a serum-free culture medium containing no TFT2 and TFT9 by the time five days have passed since the start of the adherent culturing. It is preferable to add CNTF continuously from beginning to end of the culturing. This makes it possible to ensure that the differentiation into retinal nerve cells is induced in about two weeks from the start of the adherent culturing. Further, it is preferable to further add a commercially available N2 supplement to the serum-free culture medium.

The growth factor which is used in the adherent culturing step S13 and is added to the serum-free culture medium is not limited to these described above. It may be for example an FGF family member other than FGF2 and FGF9, EGF (epidermal growth factor), BDNF (brain derived nutritional factor), EGF (epidermal growth factor), NT-3 (neurotrophin-3), NT-4 (neurotrophin-4), RA (retinoic acid: vitamin A), PDGF (platelet derived growth factor), T3 (triiodothyronine), or another factor.

Further, it is preferable that a culture dish used for the adherent culturing be coated with either an extracellular matrix component (e.g., laminin or collagen) or poly D lysine. However, the culture dish for the adherent culturing is not particularly limited to this.

Further, the iris pigmented epithelial cells to be implanted on the serum-free culture medium at the start of the adherent culturing have a cell density (number of cells per $cm^2$) of $1\times10^5$ cells/$cm^2$ or less. This makes it possible to more efficiently induce the differentiation into the retinal the nerve cells. When the iris pigmented epithelial cells have a cell density of $1\times10^4$ to $5\times10^4$ cells/$cm^2$, the differentiation into the retinal nerve cells is further more efficiently induced.

The culturing in the adherent culturing step S13 may be conducted under publicly known conventional conditions for neural stem/progenitor-cell culturing, except these conditions described above.

By using a publicly known conventional general neural marker to detect the nerve cells therein, it is possible to confirm whether or not the differentiation into various nerve cells (such as neurons, astrocytes, oligodendrocytes, and the like) is induced in the cells cultured under culturing conditions as described above. A tubulin or a neurofilament may be used as a marker to detect neurons. GFAP or the like may be used as a marker to detect astrocytes. O4 or the like may be used as a marker to detect oligodendrocytes.

Moreover, after neurons, astrocytes, and oligodendrocytes are detected, specific-antibody staining of a marker protein (which is a character specific to retinal nerve cells) is conducted so as to detect the marker protein in each of the three types of nerve cells. In this way, it is possible to check whether or not the differentiation of the nerve cells into retinal nerve cells has been induced and thereby the retinal nerve cells have been produced. Further, also by using an RT-PCR method to confirm expression of a marker gene in RNA extracted from differentiated cells, in addition to conducting antibody staining of the marker protein, it can be confirmed whether the retinal nerve cells have been produced or not.

As the marker protein, rhodopsin or iodopsin described in the First Embodiment can be exemplified. These proteins are specifically expressed in retinal visual cells, which are a type of retinal nerve cell. Further, as retinal nerve cells other than retinal visual cells, for example, bipolar cells, Muller glia cells, and amacrine cells can be exemplified. PKC (phosphokinase) can be used as a marker protein for bipolar cells. A vimentin can be used as a marker protein for Muller glia cells. An HPC-1 can be used as a marker protein for amacrine cells.

Detection of rhodopsin and iodopsin (see FIGS. 5(*a*) and 5(*b*)) in the cells which have been subjected to adherent culturing confirms that the cultured cells have been induced into retinal visual cells. Further, detection of PKC (phosphokinase) (see FIG. 5(*c*)) in the cells which have been subjected to adherent culturing confirms that the cultured cells have been induced into bipolar cells. Detection of vimentin confirms that the cultured cells have been induced into Muller glia cells. Detection of HPC-1 confirms that the cultured cells have been induced into amacrine cells.

According to the method described above, it is possible to produce the retinal nerve cells by inducing the differentiation of the iris pigmented epithelial cells into the retinal nerve cells. Therefore, the method has a possibility of being used in such highly effective regenerative medical treatment that retinal nerve cells are produced from part of iris tissue collected from a retinal disease patient per se.

[Third Embodiment]

A Third Embodiment of the present invention will be described below. The present invention is not to be limited by the description.

Described in the Third Embodiment is a retinal-nerve-cell-producing method which includes the steps of: isolating iris pigmented epithelial cells from an eyeball; starting adherent culturing of the iris pigmented epithelial cells on a culture medium containing FGF2 and/or FGF9; and performing adherent culturing of the iris pigmented epithelial cells to by adding CNTF to the culture medium, while removing FGF2 and/or FGF9 from the culture medium, after the step of starting the adherent culturing and inducing the differentiation into the retinal nerve cells.

As with the Second Embodiment, the method according to the present embodiment for producing the retinal nerve cells mainly includes: an iris-pigmented-epithelial-cell-isolating step S11 of isolating the iris pigmented epithelial cells from the eyeball; and an adherent culturing step S13 of performing adherent culturing of the iris pigmented epithelial cells. Further, as with the Second Embodiment, the method of the Third Embodiment for producing the retinal nerve cells includes a selective culturing step S12 between the iris-pigmented-epithelial-cell-isolating step S11 and the adherent culturing step S13 (see FIG. 3).

Moreover, in the method of the Third Embodiment for producing the retinal nerve cells, the adherent culturing step S13 includes the steps of:; starting adherent culturing of the iris pigmented epithelial cells with the culture medium containing FGF2 and/or FGF9; and performing adherent culturing of the iris pigmented epithelial cells by adding CNTF to the culture medium, while removing FGF2 and/or FGF9 from the culture medium, after the step of starting the adherent culturing and inducing the differentiation into the retinal nerve cells.

The method of the Third Embodiment for producing the retinal nerve cells differs from that of the Second Embodiment in that different culture media are used in the adherent culturing step S13 and the factors are added to the culture media in different manners. Therefore, since the Third Embodiment can be conducted by the same technique as the Second Embodiment except the technique of the adherent culturing step S13, the description thereof is omitted here.

In the Third Embodiment, a culture medium used in the step of starting adherent culturing may be a serum-free culture medium, but does not need to be so limited and may include a serum. As the culture medium for adherent culturing, DMEM/F12 culture medium, DMEM culture medium, EMEM culture medium (all manufactured by Invitrogen Corporation), or the like may be used. Further, as the serum used here, for example, a fetal calf serum (FCS) can be exemplified. It is preferable that the culture medium contain the serum with a concentration of 1 to 10% (W/V).

Further, the culture medium at the start of the adherent culturing further contains FGF2 and/or FGF9. It is preferable that the FGF2 (or FGF9) in the culture medium have a concentration of 10 to 40 ng/ml.

The factor to be added to the culture medium at the start of the adherent culturing is not limited to these described above. It is for example an FGF family member other than FGF2 and FGF9, EGF, BDNF, EGF, NT-3, NT-4, RA, PDGF, T3, or the like.

Further, a culture dish used for adherent culturing is for example a culture dish coated with either an extracellular substrate component (e.g., laminin, collagen, or the like) or poly D lysine. However, it is not to be particularly limited to this.

Further, it is preferable that the iris pigmented epithelial cells to be implanted on the serum-free culture medium at the start of the adherent culturing have a cell density (number of cells per $cm^2$) of $1\times10^5$ cells/$cm^2$ or less. This makes it possible to more efficiently induce the differentiation into the retinal nerve cells.

One to three days after the start of the adherent culturing, FGF2 and/or FGF9 are/is removed from the culture medium, and CNTF is added as a factor to the culture medium. Then the culturing of the iris pigmented epithelial cells on the culture medium is continued. In this way, the differentiation into the retinal nerve cells can be induced.

If the serum-free culture medium is used in the step of starting adherent culturing, a serum (e.g., FCS) may be added to the culture medium at the same time as CNTF so that the serum has a concentration of 1 to 10% (W/V).

Except the foregoing culturing conditions, the adherent culturing step S13 of the Third Embodiment may be conducted under the same conditions as that of the Second Embodiment.

As with the Second Embodiment, by using a publicly known conventional general neural marker to detect the nerve cells therein, it is possible to confirm whether or not the differentiation into various nerve cells (such as neurons, astrocytes, oligodendrocytes, and the like) is induced in the cells cultured under culturing conditions as described above.

Furthermore, as with the Second Embodiment, specific-antibody staining of a marker protein (which is a character specific to retinal nerve cells) is conducted so as to detect the marker protein in each of the three types of nerve cells. In this way, it is possible to check whether or not the differentiation of the nerve cells into retinal nerve cells has been induced and thereby the retinal nerve cells have been produced. Further, also by using an RT-PCR method to confirm expression of a marker gene in RNA extracted from differentiated cells, in addition to conducting antibody staining of the marker protein, it can be confirmed whether the retinal nerve cells have been produced or not.

According to the method described above, it is possible to produce the retinal nerve cells by inducing the differentiation of the iris pigmented epithelial cells into the retinal nerve cells. Furthermore, according to the method of the Third Embodiment, it is possible to more quickly induce the differentiation into the retinal nerve cells. Therefore, it is possible to produce the retinal nerve cells in a shorter period of time as compared with the method of the Second Embodiment.

EXAMPLE

The present invention will be more specifically described below, but it is not to be limited by the description.
(Isolation of Iris Pigmented Epithelial Cells from Mammal)

Iris pigmented epithelial cells were extirpated from each of the following mammals: a ten-day-old mouse, a twelve-day-old mouse, and a two-month-old mouse ("C57BL6"; provided from SLC Inc. or Clare Inc.); a nine-day-old rat, a ten-day-old rat, an eleven-day-old rat, a twelve-day-old rat, a three-week-old rat, and a two-month-old rat ("DA Rat"; provided from SLC Inc.); and a nineteen-week-old human embryo (provided from the director of Kurashiki Adult Disease Center; approved by the ethical committee of the center).

Only iris tissue was extirpated from an eyeball of each of the mammals by using commercially available micro scissors. The iris tissue was allowed to react in 1000 U/mL dispase solution ("dispase" manufactured by Godo Seishu Co., Ltd.) at 37° C. for 15 to 40 minutes and then in 0.05% EDTA (ethylenediaminetetraacetic acid) solution at room temperature for 20 to 30 minutes. After the reaction, the iris tissue was allowed to react in a culture medium with 8% fetal calf serum content ("DMEM culture medium" manufactured by Invitrogen Corporation) for 30 to 60 minutes so as to restore the iris tissue. Thereafter, an iris substrate and an iris pigmented epithelium were separated by peeling and collecting only the iris pigmented epithelium from the iris tissue with use of commercially available micro forceps.

The iris tissue of the ten-day-old mouse was allowed to react in 1000 U/mL dispase solution at 37° C. for 16 minutes, then in 0.05% EDTA solution at room temperature for 20 minutes, and then in a culture medium with 8% fetal calf serum content for 90 minutes.

Further, the iris tissue of the twelve-day-old mouse was allowed to react in 1000 U/mL dispase solution at 37° C. for 20 minutes, then in 0.05% EDTA solution at room temperature for 25 minutes, and then in a culture medium with 8% fetal calf serum content for 60 minutes.

Further, the iris tissue of the two-month-old mouse was allowed to react in 1000 U/mL dispase solution at 37° C. for 30 minutes, then in 0.05% EDTA solution at room temperature for 40 minutes, and then in a culture medium with 8% fetal calf serum content for 30 minutes at room temperature.

The iris tissue of the eleven-day-old rat was allowed to react in 1000 U/mL dispase solution for 20 minutes, then in 0.05% EDTA solution for 25 minutes, and then in a culture medium with 8% fetal calf serum content for 90 minutes.

The iris tissue of the nineteen-week-old human embryo was allowed to react in 1000 U/mL dispase solution at 37° C. for 30 minutes, then in 0.05% EDTA solution at room temperature for 30 minutes, and then in a culture medium at room temperature with 8% fetal calf serum content for 60 minutes.
(Isolation of Iris Pigmented Epithelial Cells from Bird)

Iris pigmented epithelial cells were extirpated, basically in the same manner as the mammals, from each of the following birds: a one-day-old chick and a two-day-old chick (provided from Global Chick Inc. in Gifu Prefecture).

The iris tissue of the two-day-old-chick was allowed to react in 1000 U/mL dispase solution at 37° C. for 30 minutes, then in 0.05% EDTA solution for 30 minutes, and then in a culture medium with 8% fetal calf serum content for 5 minutes. The reaction treatment with use of the fetal calf serum may be omitted.

(Floated Coagulated Mass Culturing Technique)

Figure 6:
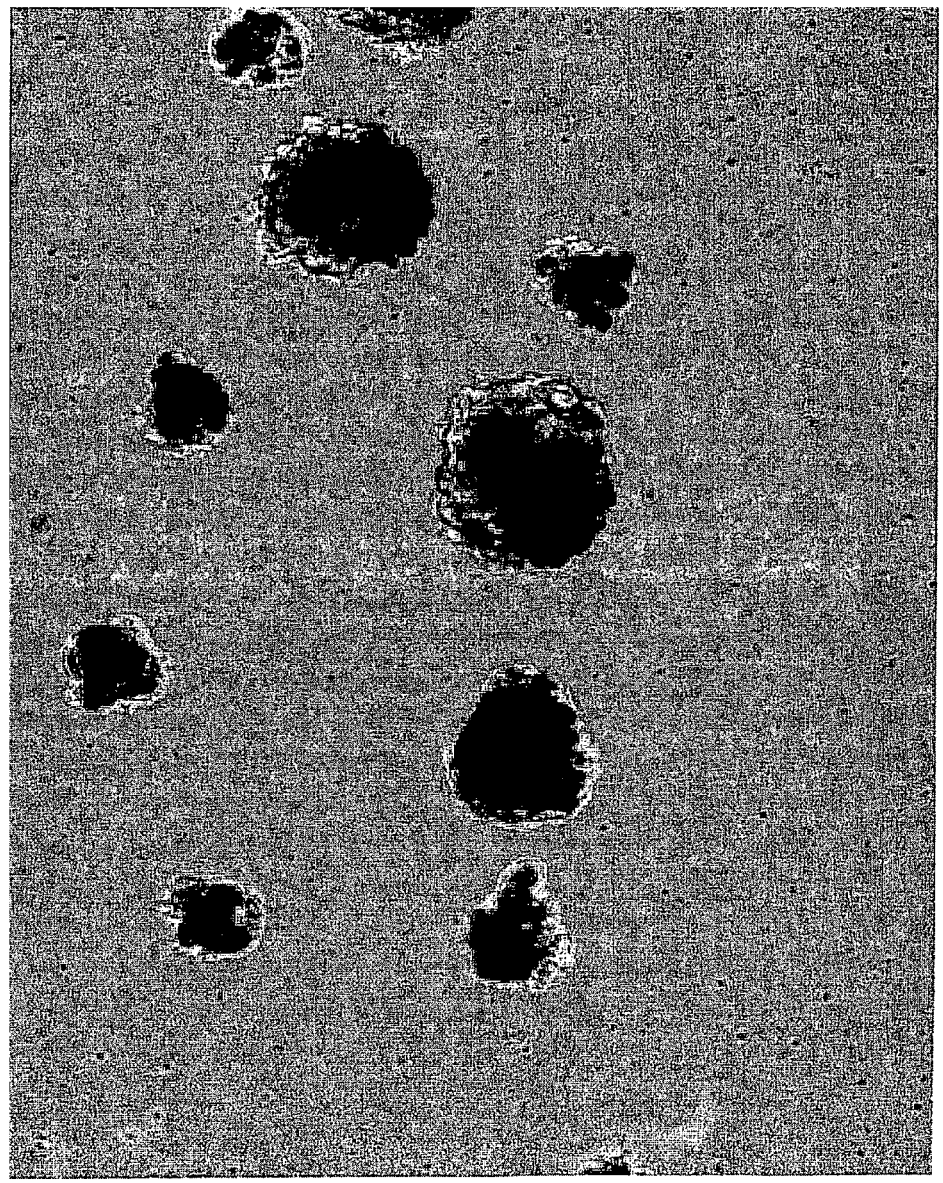
FIG. 6 is a pattern diagram illustrating an aggregate (sphere) derived from the iris pigmented epithelial cells of the chick.

The isolated iris pigmented epithelial tissue of the mammal or the bird was dissociated into cells by using a commercially available trypsin solution. Thereafter, the dissociated iris pigmented epithelial cells were selectively cultured by the neurosphere method (floated coagulated mass culturing technique) described in Reference 3. Used as a floated-coagulated-mass-culturing culture medium was a mixture of a serum-free culture medium ("DMEM/F12 culture medium" manufactured by Invitrogen Corporation) and a 1/100 volume of N2 supplement manufactured by Invitrogen Corporation. The iris pigmented epithelial cells which had been subjected to trypsin treatment was cultured in the floated-coagulated-mass-culturing culture medium while rotated by using a commercially available shaker. This made it possible to obtain aggregates similar to aggregates (spheres) made from neural stem/progenitor cells derived from a brain or a spinal cord (see FIG. 6).

(Induction of Differentiation of Iris Pigmented Epithelial Cells into Retinal Nerve Cells by Co-Culturing)

In accordance with the process described in Reference 4, passage of embryonic retinal stem cells of a chicken was carried out by culturing the embryonic retinal stem cells together with iris pigmented epithelial cells (neural stem/progenitor cells derived from iris tissue) isolated from and dissociated from an eyeball of a mouse by the process described above.

Specifically, isolation of a mouse iris and culturing of iris pigmented epithelial cells were conducted in accordance with the procedure described above. After three to six days of culturing, the iris pigmented epithelial cells were dissociated with a mixed solution of dispase and trypsin. The passage of the dissociated iris pigmented epithelial cells was carried out in the inner well 2 together with the embryonic retinal stem cells of the chicken by rotation culturing (see FIG. 2).

After fourteen days of culturing, the cultured cells were collected.

Figure 4A:
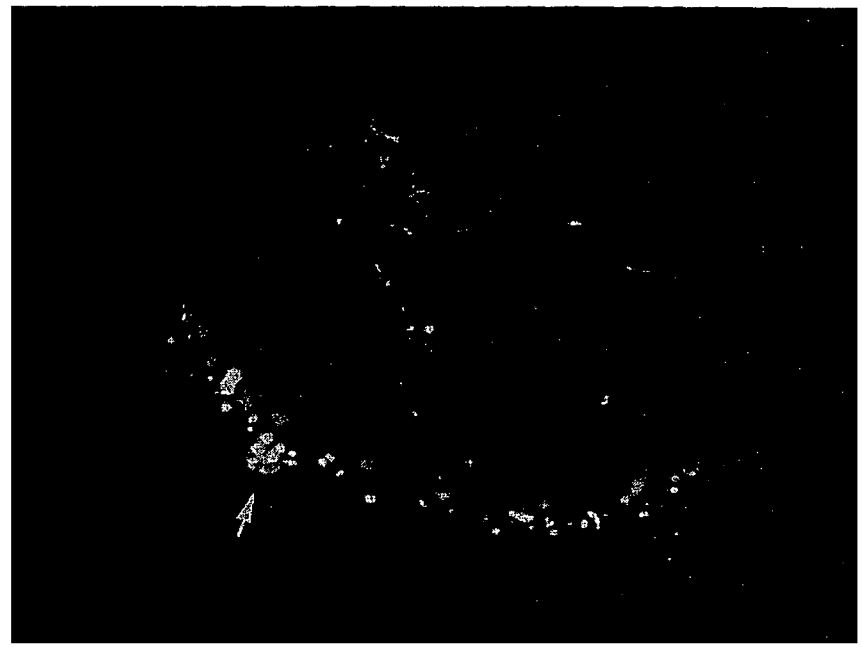
FIG. 4(a) is a pattern diagram illustrating rhodopsin positive cells derived from iris pigmented epithelial cells of a mouse. The arrow indicates rhodopsin subjected to immunostaining in an Example.
Figure 4B:
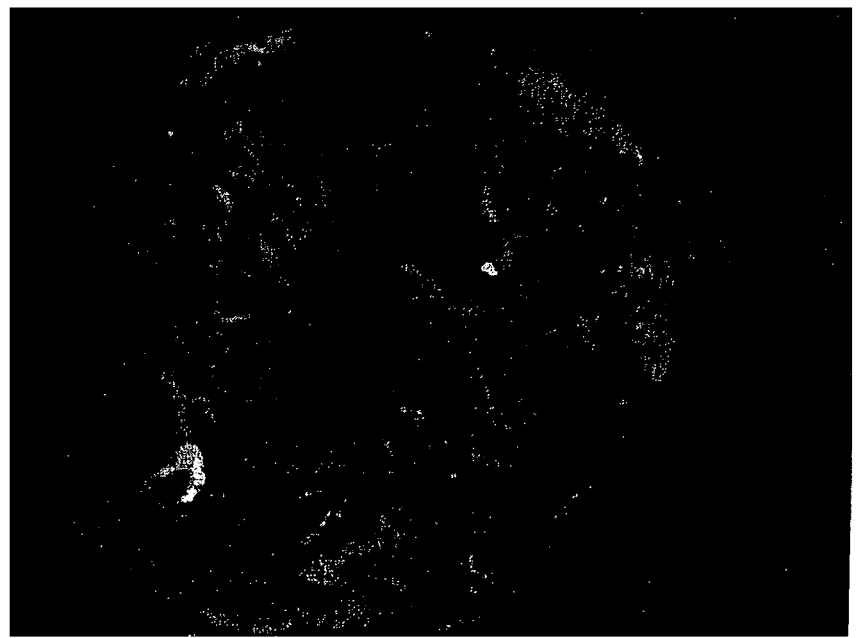
FIG. 4(b) is a pattern diagram illustrating vimentin positive cells derived from the iris pigmented epithelial cells of the mouse. The white area indicates vimentin subjected to immunostaining in the Example.

Subsequently, by conducting immunostaining of a marker protein specific for retinal nerve cells, it was confirmed whether differentiation of the cultured cells into the retinal nerve cells had been induced. As a result, as illustrated in FIGS. 4(a) and 4(b), rhodopsin (indicated by the arrow in FIG. 4(a)), which is a highly specific protein for exhibiting a photoreceptor function, and vimentin (indicated by the white area in FIG. 4(b)), which is a protein specific for Muller glia cells, were detected in the cultured cells. Rhodopsin is a protein necessary for a retinal visual cell to exhibit the photoreceptor function and is specifically expressed in a rod forming the retinal visual cell.

The detection of the rhodopsin in the cultured cells proved that the cultured cells have been differentiated into retinal nerve cells (more specifically, retinal visual cells). Further, the detection of the vimentin in the cultured cells proved that the cultured cells have also been differentiated into retinal nerve cells (more specifically, Muller glia cells).

Example 1

Differentiation Induction into Retinal Nerve Cells by Adherent Culturing

Described in Example 1 is an experiment on differentiation induction into retinal nerve cells. In Example 1, the adherent culturing iris pigmented epithelial cells was carried out with a serum-free culture medium.

Passage of Iris pigmented epithelial cells of a chick, which carried out on a laminin-coated dish, the Iris pigmented epithelial cells isolated and dissociated by the process described above. A mixture of DMEM/F12 culture medium, N2 supplement, and growth factor FGF2 (20 ng/ml) was used as a culture medium. The iris pigmented epithelial cells at this time had a cell density $3.2 \times 10^4$ cells/cm$^2$. Further, although the growth factor FGF2 was used in the present example, a growth factor FGF9 may be used instead of the growth factor FGF2.

Four to five days after the start of culturing, growth factor FGF2 stopped being added. The culturing was continued for two to seven more days. As a result, it was confirmed that the iris pigmented epithelial cells were changed into neurocyte-like form.

After about two weeks of serum-free culturing, the cultured cells were collected. Detection of nerve cells in the cultured cells was carried out by using general neural markers such as a tubulin (or neurofilament), GFAP, and O4. As a result, because the various neural markers were detected, it was confirmed that the cultured cells were differentiated into the nerve cells (specifically neurons, astrocytes, and oligodendrocytes).

Figure 5A:
FIG. 5(a) is a pattern diagram illustrating rhodopsin positive cells derived from iris pigmented epithelial cells of a chick. The white area indicates rhodopsin subjected to immunostaining in the Example.
Figure 5B:
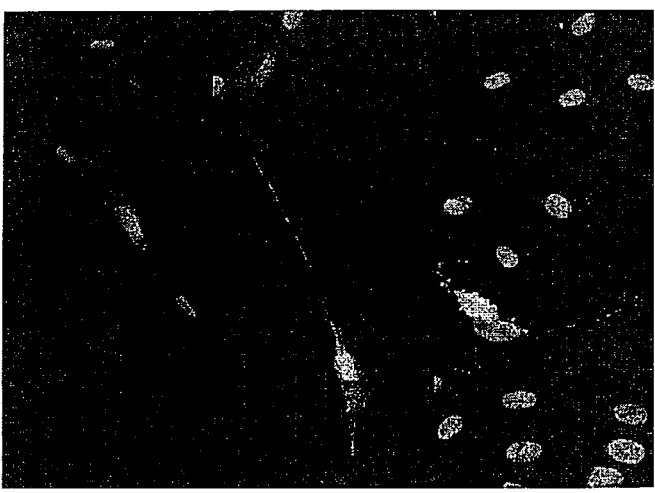
FIG. 5(b) is a pattern diagram illustrating iodopsin positive cells derived from the iris pigmented epithelial cells of the chick. The white area indicates iodopsin subjected to immunostaining in the Example.
Figure 5C:
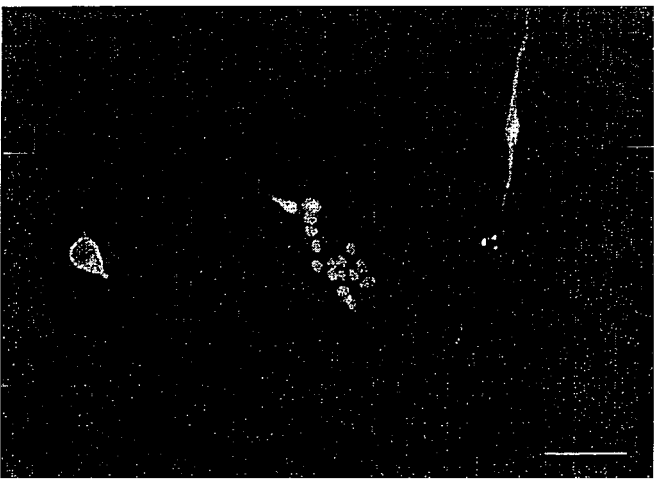
FIG. 5(c) is a pattern diagram illustrating PKC positive cells derived from the iris pigmented epithelial cells of the chick. The white area indicates PKC subjected to immunostaining in the Example.

Subsequently, by conducting immunostaining of a marker protein specific for retinal nerve cells, it was confirmed whether differentiation of the cultured cells into the retinal nerve cells had been induced. As a result, as illustrated in FIGS. 5(a) to 5(c), rhodopsin (indicated by the white area in FIG. 5(a)), iodopsin (indicated by the white area in FIG. 5(b)), and PKC (indicated by the white area in FIG. 5(c)) were detected in the cultured cells. Rhodopsin and Iodopsin are expressed specifically in retinal visual cells. Further, PKC is expressed specifically in bipolar cells.

The detection of rhodopsin, iodopsin, and PKC in the cultured cells proved that the cultured cells were differentiated into retinal neural cells, namely retinal visual cells and bipolar cells.

Since rhodopsin, iodopsin, and PKC were used as makers for detecting retinal nerve cells, induction of retinal visual cells and bipolar cells was confirmed. However, there is a possibility that other retinal nerve cells were contained in the cultured cells.

Example 2

Differentiation Induction into Retinal Nerve Cells by Adherent Culturing

Described in Example 2 is an experiment on differentiation induction into retinal nerve cells in the case where adherent culturing of iris pigmented epithelial cells is carried out with a serum-containing culture medium.

Passage of iris pigmented epithelial cells of a chick, which were isolated and dissociated by the process described above, was carried out on a laminin-coated dish. A mixture of DMEM/F12 culture medium, N2 supplement, growth factor FGF2 (20 ng/ml), and fetal calf serum (FCS; 1% (W/V)) was used as a culture medium. The iris pigmented epithelial cells at this time had a cell density $3.2 \times 10^4$ cells/cm$^2$. Further, the growth factor FGF2 was used in the present example, a growth factor FGF9 may be used instead of the growth factor FGF2.

One to three days after the start of culturing, growth factor FGF2 stopped being added, and CNTF (10 to 30 ng/ml) was added. The culturing was continued for two to seven more days. As a result, it was confirmed that the iris pigmented epithelial cells were changed into neurocyte-like form.

After about one week of serum-free culturing, the cultured cells were collected. Detection of nerve cells was carried out by using general neural markers such as tubulin (or neurofilament), GFAP, and O4. As a result, because the various neural markers were detected, it was confirmed that the cultured cells were differentiated into the nerve cells (specifically neurons, astrocytes, and oligodendrocytes).

Figure 7A:
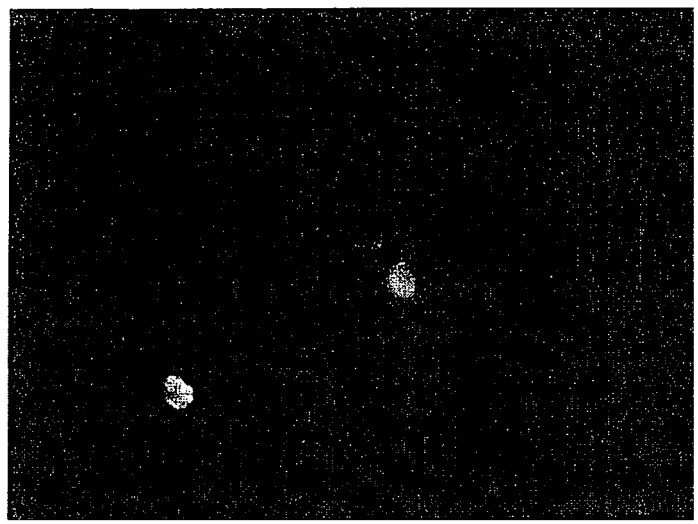
FIG. 7(*a*) is a pattern diagram illustrating rhodopsin positive cells derived from the iris pigmented epithelial cells of the chick. The white area indicates rhodopsin subjected to immunostaining in the Example.
Figure 7B:
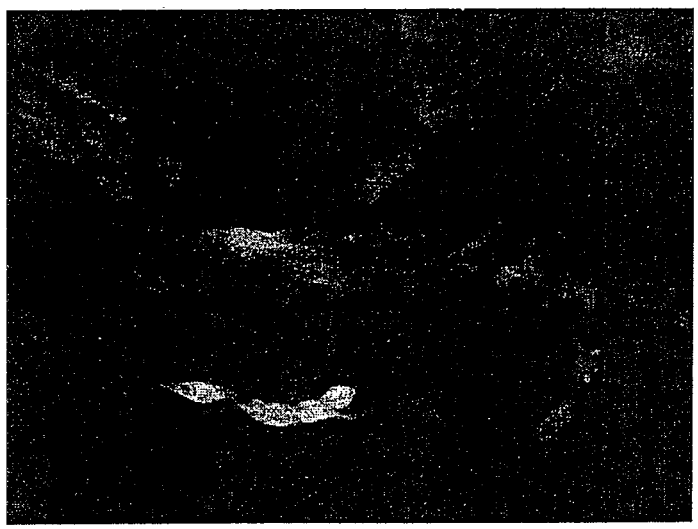
Figure 7C:

Subsequently, by conducting immunostaining of a marker protein specific for retinal nerve cells, it was confirmed whether differentiation of the cultured cells into the retinal nerve cells had been induced. As a result, as illustrated in FIGS. 7(a) to 7(c), rhodopsin (indicated by the white area in FIG. 7(a)), iodopsin (indicated by the white area in FIG. 7(b)), and HPC-1 (indicated by the white area in FIG. 7(c)) were detected from the cultured cells. Rhodopsin and iodopsin are expressed specifically in retinal visual cells. Further, HPC-1 is expressed specifically in amacrine cells.

The detection of rhodopsin, iodopsin, and HPC-1 in the cultured cells proved that the cultured cells were differentiated into retinal neural cells, namely retinal visual cells and amacrine cells.

Further, in Example 2, iris pigmented epithelial cells of a young mouse were isolated and dissociated by the process described above and subjected to differentiation induction as with the chick case. Detection of various cells in the cultured cells obtained by the experiment carried out by using various retinal neural markers (PKC, HPC-1, rhodopsin). The result is shown below in Table 1.

TABLE 1

Detection of Retinal Nerve Cells Derived from
Iris Pigmented Epithelial Cells of Mouse

| Names of Retinal Neural Markers | Detection Status (Those retinal neural markers found positive by specific-antibody staining are marked with ○) |
|---|---|
| PKC | ○ |
| HPC-1 | ○ |
| Rhodopsin | ○ |

As shown in Table 1, PKC, HPC-1, and rhodopsin were detected in the cultured cells. This proved that the cultured cells were differentiated into retinal nerve cells, namely bipolar cells, amacrine cells, and retinal visual cells.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, according to the methods of the present invention, it is possible to produce retinal nerve cells of a mammal for which no conventional effective retinal-nerve-cell-differentiation-inducing method has been found. Since mammals includes many animal species, such as human beings, which serve many uses, the methods which makes it possible to produce the retinal nerve cells of the mammal are expected to contribute to development of the fields of medicine, biotechnology, and the like.

Since the retinal nerve cells of the present invention are produced from iris pigmented epithelial cells part of which can be collected from a patient per se, regenerative medical treatment using cells of a patient per se can be realized. Moreover, it is expected to make it possible to overcome such problems of regenerative medical treatment as immunological rejection, ethical issues, and unbalance between the demand and supply of transplant cell sources. Furthermore, it is also expected to contribute to establishing a treatment for a retinal degeneration disease for which there is no effective treatment at present.

Further, the retinal nerve cells of the present invention are produced by inducing differentiation without gene transfer. Therefore, the present invention does not pose a risk such as DNA damage and ensures safety when used for medical purposes.

The invention claimed is:

1. A method for producing rhodopsin-positive retinal nerve cells, the method comprising the steps of:
   isolating iris pigmented epithelial cells from an eyeball;
   selectively culturing the iris pigmented epithelial cells isolated from the eyeball by a floated coagulated mass culturing technique; and
   performing adherent culturing of the iris pigmented epithelial cells obtained in the selectively culturing step with a serum-free culture medium so as to induce differentiation of the iris pigmented epithelial cells into the rhodopsin-positive retinal nerve cells, the iris pigmented epithelial cells not being subjected to a gene transfer,
   the serum-free culture medium containing at least one of a fibroblast growth factor 2, a fibroblast growth factor 9, and a ciliary neurotrophic factor with a concentration in a range of 1 to 100 ng/mL,
   the iris pigmented epithelial cells in the serum-free culture medium when the adherent culturing starts having a cell density of $1 \times 10^5$ cells/cm$^2$ or less,
   the serum-free culture medium being a DMEM/F12 culture medium, a DMEM culture medium, or an EMEM culture medium.

2. The method according to claim 1, wherein the iris pigmented epithelial cells are derived from a bird or a mammal.

3. The method according to claim 1, wherein the fibroblast growth factor 2 and the fibroblast growth factor 9 stop being added after two to five days from the start of the adherent culturing, and the ciliary neurotrophic factor is continuously added from the start of the adherent culturing to the end of the adherent culturing.

4. The method according to claim 1, wherein the iris pigmented epithelial cells are derived from an adult mammal.

* * * * *